US010048285B2

(12) United States Patent
Ohfuchi et al.

(10) Patent No.: US 10,048,285 B2
(45) Date of Patent: Aug. 14, 2018

(54) SAMPLE PROCESSING APPARATUS

(71) Applicant: SYSMEX CORPORATION, Kobe-shi, Hyogo (JP)

(72) Inventors: Masashi Ohfuchi, Kobe (JP); Yusuke Matsumoto, Kobe (JP)

(73) Assignee: SYSMEX CORPORATION, Kobe-shi (JP)

( * ) Notice: Subject to any disclaimer, the term of this patent is extended or adjusted under 35 U.S.C. 154(b) by 356 days.

(21) Appl. No.: 14/868,850

(22) Filed: Sep. 29, 2015

(65) Prior Publication Data

US 2016/0091519 A1 Mar. 31, 2016

(30) Foreign Application Priority Data

Sep. 30, 2014 (JP) ................................ 2014-201079

(51) Int. Cl.
*G01N 35/10* (2006.01)
*B25J 9/16* (2006.01)
*G01N 35/00* (2006.01)

(52) U.S. Cl.
CPC ........ *G01N 35/1002* (2013.01); *B25J 9/1679* (2013.01); *G01N 35/00584* (2013.01); *G01N 35/1083* (2013.01)

(58) Field of Classification Search
CPC ......... G01N 35/1002; G01N 35/00584; G01N 35/1083; B25J 9/1679
See application file for complete search history.

(56) References Cited

U.S. PATENT DOCUMENTS

| 8,778,268 B2 | 7/2014 | Takehara et al. |
| 2009/0215183 A1* | 8/2009 | Takehara ......... C01N 35/00623 436/47 |
| 2013/0131859 A1* | 5/2013 | Takai ................. G01N 35/0092 700/214 |

FOREIGN PATENT DOCUMENTS

| JP | 2000-235037 A | 8/2000 |
| JP | 2008-151594 A | 7/2008 |
| JP | 2009-204386 A | 9/2009 |
| WO | 2011/089966 A1 | 7/2011 |

* cited by examiner

*Primary Examiner* — Samuel P Siefke
(74) *Attorney, Agent, or Firm* — Metrolexis Law Group PLLC

(57) ABSTRACT

Disclosed is a sample processing apparatus, comprising: a first mechanism unit having a first operation range of movement and that carries out a first process on a container with a sample, the first operation range comprising an overlap region and a non-overlap region; a second mechanism unit having a second operation range of movement and that carries out a second process on the container after completion of the first process, the second operation range comprising the overlap region but not the non-overlap region; an operation detector that senses operation of the first mechanism unit; and a controller that causes the first mechanism unit to stop the first process and retreat from the overlap region and that causes the second mechanism unit to continue the second process upon detection of abnormality in the first mechanism unit based on the detection result by the operation detector.

17 Claims, 12 Drawing Sheets

Fig. 7 FLOW OF OPERATION IN MEASURING PROCESS

Fig. 8 FLOW OF R3 REAGENT DISPENSING OPERATION

SAMPLE PROCESSING APPARATUS

CROSS REFERENCE TO RELATED APPLICATIONS

This application claims priority to prior Japanese Patent Application No. 2014-201079 filed on Sep. 30, 2014 entitled "SAMPLE PROCESSING APPARATUS," the entire contents of which are hereby incorporated by reference.

BACKGROUND

This disclosure relates to an abnormality responding process in a sample processing apparatus.

Japanese Patent Application Publication No. 2009-204386 (Patent Literature 1) discloses a sample processing apparatus including a first mechanism unit that performs an upstream process step and a second mechanism unit that performs a downstream process step. When an abnormality occurs in the first mechanism unit, this sample processing apparatus performs an abnormality responding process which causes the first mechanism unit to stop and the second mechanism unit to continue its operation. The first mechanism unit and the second mechanism unit are arranged away from each other to avoid overlap between their operation ranges.

In Patent Literature 1, the first mechanism unit and the second mechanism unit need to be spaced from each other to avoid overlap between their operation ranges in order to prevent operation interference by the first mechanism unit when the first mechanism unit is stopped due to its abnormality. This results in restrictions on the layout of components of the sample processing apparatus including the first mechanism unit and the second mechanism unit. Thus, it is desired to improve the freedom in layout.

SUMMARY

An embodiment of a sample processing apparatus, comprising: a first mechanism unit having a first operation range of movement and that carries out a first process on a container with a sample, the first operation range comprising an overlap region and a non-overlap region; a second mechanism unit having a second operation range of movement and that carries out a second process on the container after completion of the first process, the second operation range comprising the overlap region but not the non-overlap region; an operation detector that senses operation of the first mechanism unit; and a controller that causes the first mechanism unit to stop the first process and retreat from the overlap region and that causes the second mechanism unit to continue the second process upon detection of abnormality in the first mechanism unit based on the detection result by the operation detector.

DETAILED DESCRIPTION

An embodiment is described below based on the drawings.

The configuration of sample processing apparatus 100 according to this embodiment is described with reference to FIGS. 1 to 13.

General Configuration of Sample Processing Apparatus

Figure 1:
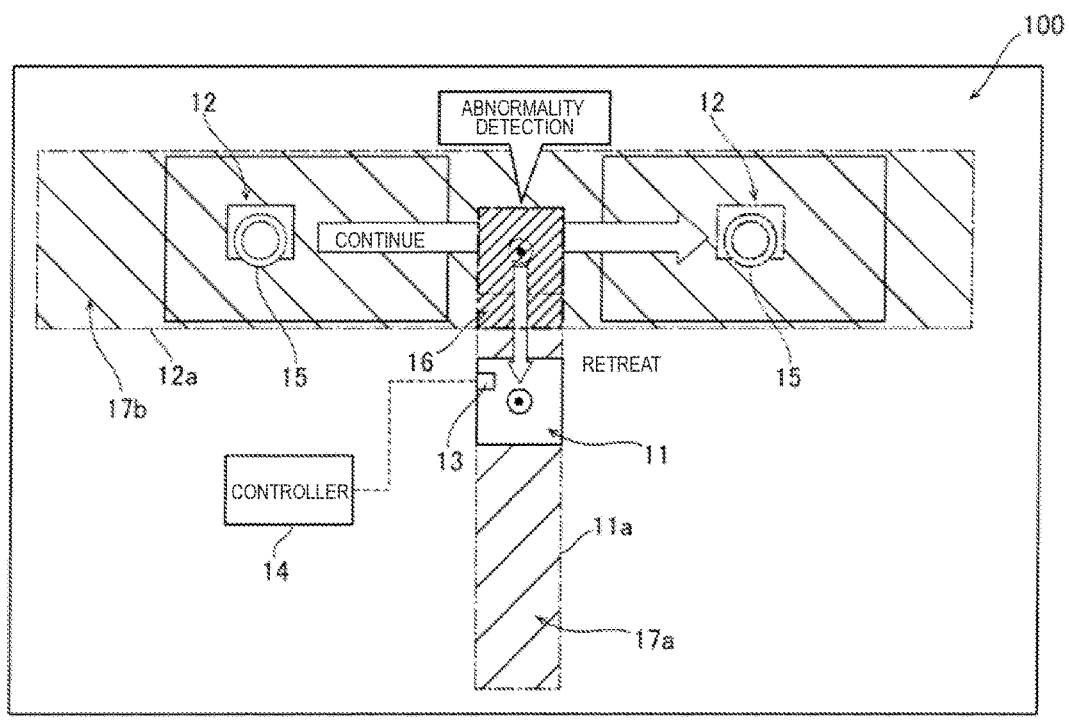
FIG. 1 is a schematic plan view illustrating the general configuration of a sample processing apparatus according to an embodiment.

As illustrated in FIG. 1, sample processing apparatus 100 includes first mechanism unit 11, second mechanism unit 12, operation detector 13, and controller 14. Sample processing apparatus 100 is an apparatus that analyzes a sample by sequentially performing processes on container 15 containing the sample.

First mechanism unit 11 is capable of performing a first process on container 15 containing the sample. Second mechanism unit 12 is capable of performing a second process on container 15 after completion of the first process. In other words, first mechanism unit 11 performs a process step at a stage upstream of second mechanism unit 12, and second mechanism unit 12 performs a process step at a stage downstream of first mechanism unit 11.

First mechanism unit 11 is capable of moving within first operation range 11a, including overlap region 16 and non-overlap region 17a. Second mechanism unit 12 is capable of moving within second operation range 12a including overlap region 16 and not overlapping non-overlap region 17a.

First operation range 11a and second operation range 12a overlap each other at overlap region 16. On the other hand, non-overlap region 17a of first operation range 11a and non-overlap region 17b of second operation range 12a do not overlap each other. Thus, only one of first mechanism unit 11 and second mechanism unit 12 can enter overlap region 16.

Operation detector 13 is capable of detecting the operation of first mechanism unit 11. Operation detector 13 can include various types of sensors. Operation detector 13 may include a position sensor or a switch which detects that first mechanism unit 11 has moved to a predetermined position in first operation range 11a. Alternatively, operation detector 13 may include a detector which detects that first mechanism unit 11 has collided (contacted) with an object as a result of its operation in the first process. Operation detector 13 employs a configuration which is appropriate for the first process which first mechanism unit 11 performs.

Controller 14 controls the operations of first mechanism unit 11 and second mechanism unit 12. Controller 14 is capable of obtaining a detection signal from operation detector 13 and detecting an abnormality in first mechanism unit 11 based on the result of detection by operation detector 13. Controller 14 is capable of performing control which causes first mechanism unit 11 to stop the first process and to retreat from overlap region 16 and causes second mechanism unit 12 to continue the second process upon detection of an abnormality in first mechanism unit 11. Thus, even when an abnormality occurs in first mechanism unit 11, those containers 15 for which the first process has already been completed by the time of the occurrence of the abnormality still undergo the processes in the downstream steps including the second process and are subjected to analysis.

Thus, although first mechanism unit 11 and second mechanism unit 12 are arranged with their operation ranges overlapping each other, first mechanism unit 11 can retreat from overlap region 16 to non-overlap region 17a when an abnormality occurs in first mechanism unit 11. Hence, even when an abnormality occurs in an upstream process step, the downstream process steps can be continued. Also, first mechanism unit 11 and second mechanism unit 12 do not need to be spaced from each other for preventing interference therebetween, which makes it possible to improve the freedom in the layout of first mechanism unit 11 and second mechanism unit 12, which perform these process steps.

Preferably, controller 14 stops the operations of both first mechanism unit 11 and second mechanism unit 12 upon detection of an abnormality in first mechanism unit 11 during the retreating operation of first mechanism unit 11 toward non-overlap region 17a. Specifically, controller 14 stops the operations of both first mechanism unit 11 and second mechanism unit 12 if first mechanism unit 11 performs its retreating operation upon detection of an abnormality in first mechanism unit 11 but an abnormality has occurred during the retreating operation which prevents proper completion of the retreating operation. Thus, upon occurrence of an abnormality which prevents completion of the retreating operation to non-overlap region 17a, the operation not only of first mechanism unit 11 but also of second mechanism unit 12 is stopped so that operation interference of the first mechanism unit 11 and second mechanism unit 12 with other mechanisms associated with first mechanism unit 11 and second mechanism unit 12 can be prevented reliably and quickly.

Details of Configuration of Sample Processing Apparatus

Details of the configuration of sample processing apparatus 100, which is illustrated in FIG. 1, will be specifically described below with reference to FIG. 2 and the following figures.

In the embodiment, sample processing apparatus 100 is an immune analyzer for measurement of an antigen, an antibody, or the like in a measurement-target sample. The sample is a blood specimen such as serum. Note that sample processing apparatus 100 may be a sample processing apparatus other than the immune analyzer. Though description is omitted, sample processing apparatus 100 may be a clinical sample analyzer such as a blood coagulation measuring apparatus, a urine formed element analyzer, a gene amplification measuring apparatus, or a biochemical analyzer, for example.

Figure 2:
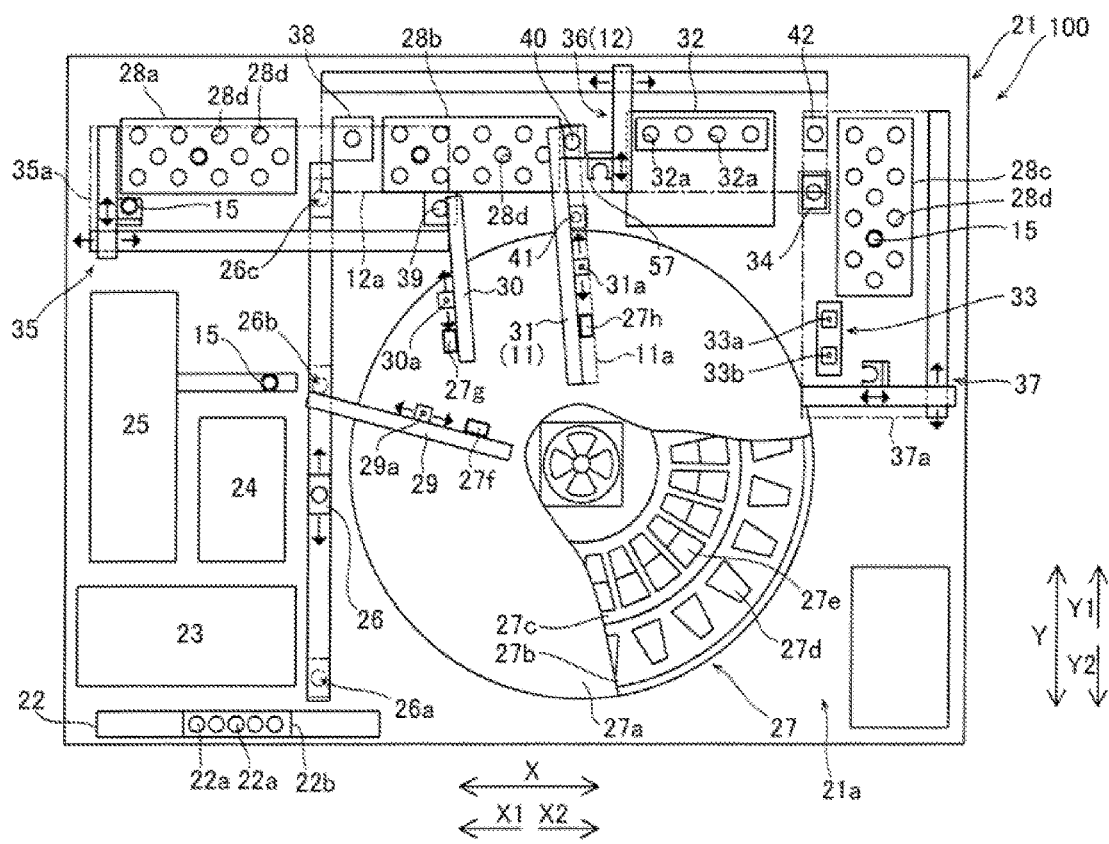
FIG. 2 is a schematic plan view illustrating a first level of the sample processing apparatus according to an embodiment.

As illustrated in FIG. 2, sample processing apparatus 100 includes housing 21, sample transporting mechanism 22, sample dispensing mechanism 23, tip supplying mechanism 24, container supplying mechanism 25, container transporter 26, reagent holder 27, reaction parts 28a to 28c, first reagent dispensing mechanism 31, second reagent dispensing mechanism 30, third reagent dispensing mechanism 29, separation process part 32, R4-R5 reagent dispensing mechanism 33, and inter-level transporter 34. Sample processing apparatus 100 also includes container transferring mechanisms 35, 36, and 37 that transfer containers 15 to these components.

In the embodiment, first mechanism unit 11 includes first reagent dispensing mechanism 31 while second mechanism unit 12 includes container transferring mechanism 36. Thus, even when an abnormality occurs in first reagent dispensing mechanism 31, those containers 15 for which the dispensing processes have already been completed before the occurrence of the abnormality can be transferred to the downstream process step by container transferring mechanism 36. First mechanism unit 11 and second mechanism unit 12 may include other mechanisms. Other specific examples of first mechanism unit 11 and second mechanism unit 12 are described later.

Housing 21 has a rectangular shape in a plan view. Housing 21 houses each component of sample processing apparatus 100 such as first mechanism unit 11 and second mechanism unit 12. Housing 21 has first level 21a (see FIG. 2), second level 21b (see FIG. 4) situated under first level 21a, and third level 21c (see FIG. 5) situated under second level 21b. In other words, housing 21 has a multi-level structure with multiple levels in the vertical direction. Note that housing 21 may be formed to have one or two levels or four or more levels. In the following, for convenience, a horizontal direction along the long sides of housing 21 is referred to as the X direction, a horizontal direction along the short sides of housing 21 is referred to as the Y direction, and the vertical direction, which is perpendicular to the X direction and the Y direction, is referred to as the Z direction.

First, the configuration of each component set at first level 21a is described with reference to FIG. 2.

Sample transporting mechanism 22 is capable of transporting rack 22b in which test tubes 22a each containing a sample are set to a predetermined sample aspirating position. Sample dispensing mechanism 23 is capable of aspirating the sample in test tube 22a and dispensing the aspirated sample into container 15 disposed at sample dispensing position 26a. Container 15 is a reaction chamber (cuvette) in which the sample therein is reacted with reagents. At the time of dispensing a sample, sample dispensing mechanism 23 attaches a disposable pipette tip (not illustrated) thereto which is supplied by tip supplying mechanism 24.

Container supplying mechanism 25 is capable of housing a number of containers 15 and supplying containers 15 one by one to container transporter 26. Container transporter 26 is capable of holding container 15 supplied from container supplying mechanism 25 and transporting it to sample dispensing position 26a, R1 reagent dispensing position 26b, and container unloading position 26c.

Reagent holder 27 includes case 27a of a cylindrical shape and reagent setting parts 27b and 27c of circular annular shapes. Reagent holder 27 is a refrigerator that cools reagents set inside case 27a, which has a heat insulation function, by mean of a cooling mechanism.

Reagent setting parts 27b and 27c of the circular annular shapes are concentrically arranged and capable of rotating independently of each other. Reagent setting part 27b on the outer periphery side is capable of holding reagent containers 27d. Each reagent container 27d contains an R2 reagent. The R2 reagent includes magnetic particles which bind to a capture antibody. Reagent setting part 27c on the inner periphery side is capable of holding reagent containers 27e. Each reagent container 27e has two partitioned reagent containing spaces therein, and the two reagent containing spaces contain an R1 reagent and an R3 reagent, respectively. The R1 reagent includes a capture antibody which binds to an antigen included in the sample. The R3 reagent includes a labeled antibody which binds to the complex of the antigen, the capture antibody and the magnetic particle. By rotating reagent setting parts 27b and 27c, reagent containers 27d and 27e are positioned at their respective predetermined reagent aspirating positions. Three aspirating holes 27f, 27g, and 27h, which are openable and closable, are provided in the upper surface of case 27a for aspirating the R1 to R3 reagents, respectively.

Each of three reaction parts 28a to 28c has the function of holding containers 15 and causing the samples and the reagents contained in containers 15 to react with each other. Specifically, each of reaction parts 28a to 28c has container holding holes 28d and is capable of heating the specimens contained in containers 15 set in container holding holes 28d.

Reaction part 28a performs a first reaction process on the specimen in each container 15 after the dispensing of the sample and the R1 reagent, and a second reaction process on the specimen after the dispensing of the R2 reagent. Between reaction part 28a and reaction part 28b, there is magnetic gathering port 38 that holds container 15 in a holding hole to gather magnetic particles in the specimen in container 15 by means of a magnet. Magnetic gathering port 38 is situated in an overlap region where operation range 35a of container transferring mechanism 35 and second operation range 12a of container transferring mechanism 36 overlap each other. Container 15 is passed from container transferring mechanism 35 to container transferring mechanism 36 at magnetic gathering port 38.

Reaction part 28b is situated between reaction part 28a and separation process part 32. Reaction part 28b performs a third reaction process on each specimen after the dispensing of the R3 reagent. R2 dispensing port 39 is provided between reaction part 28b and reagent holder 27. R3 dispensing port 40 is provided between reaction part 28b and separation process part 32. R2 dispensing port 39 is situated in an overlap region where operation range 35a of container transferring mechanism 35 and the operation range of second reagent dispensing mechanism 30 overlap each other. R3 dispensing port 40 is situated in overlap region 16 (see FIG. 3) where second operation range 12a of container transferring mechanism 36 and first operation range 11a of first reagent dispensing mechanism 31 overlap each other.

Reaction part 28c performs a fourth reaction process on each specimen after the dispensing of later-described R4 reagent and R5 reagents.

First reagent dispensing mechanism 31, second reagent dispensing mechanism 30, and third reagent dispensing mechanism 29 each have the function of performing a dispensing process of dispensing a reagent into container 15. Third reagent dispensing mechanism 29 is capable of moving between aspirating hole 27f, which is a reagent aspirating position, and reagent dispensing position 26b. Third reagent dispensing mechanism 29 includes pipette 29a that aspirates and discharges the reagent. Pipette 29a aspirates the R1 reagent from reagent container 27e in reagent holder 27 and dispenses the R1 reagent into container 15 at R1 reagent dispensing position 26b.

Second reagent dispensing mechanism 30 is capable of moving between aspirating hole 27g, which is a reagent aspirating position, and R2 dispensing port 39, which is a reagent dispensing position. Second reagent dispensing mechanism 30 includes pipette 30a that aspirates and discharges the reagent. Pipette 30a aspirates the R2 reagent from reagent container 27d in reagent holder 27 and dispenses the R2 reagent into container 15 transported to R2 dispensing port 39.

Figure 3:
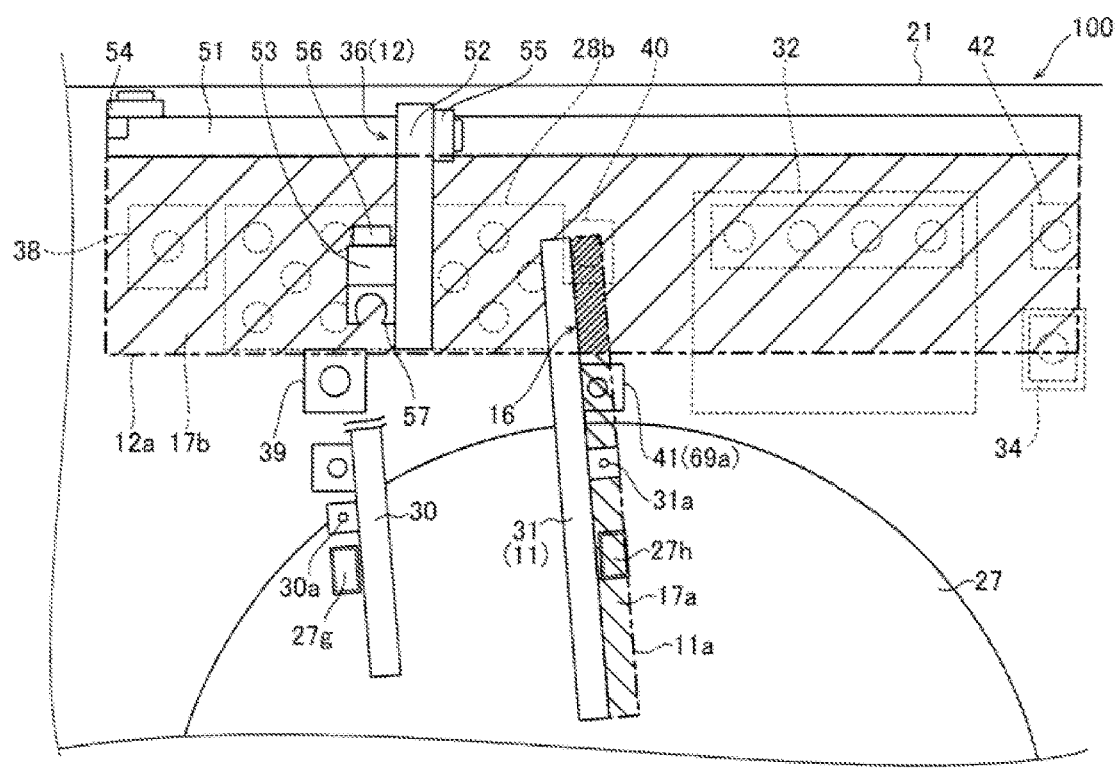
FIG. 3 is a partially enlarged view for describing the operation ranges of a container transferring mechanism and a reagent dispensing mechanism in FIG. 2.

As illustrated in FIG. 3, first reagent dispensing mechanism 31 is capable of moving within first operation range 11a between aspirating hole 27h, which is a reagent aspirating position, and R3 dispensing port 40, which is a reagent dispensing position. First reagent dispensing mechanism 31 includes pipette 31a that aspirates and discharges the reagent. Pipette 31a aspirates the R3 reagent from reagent container 27e (see FIG. 2) in reagent holder 27 and dispenses the R3 reagent into container 15 transported to R3 dispensing port 40. A cleaner 41 is provided between aspirating hole 27h and R3 dispensing port 40. Cleaner 41 is supplied with cleaning liquid. Cleaner 41 cleans the inside and outside of pipette 31a after the dispensing process. Aspirating hole 27h and cleaner 41 are situated in non-overlap region 17a.

Referring back to FIG. 2, separation process part 32 is arranged between reaction part 28b and reaction part 28c. Separation process part 32 has the function of performing a BF separation process which separates the unreacted components of the sample and the reagents from container 15. Separation process part 32 includes processing ports 32a in each of which container 15 can be set. In this embodiment, four processing ports 32a are provided. At two processing ports 32a on the reaction part 28b side, a primary BF separation process is performed on containers 15 after the dispensing of the R2 reagent. At two processing ports 32a on the reaction part 28c side, a secondary BF separation process is performed on containers 15 after the dispensing of the R3 reagent.

Junction part 42 is provided between separation process part 32 and reaction part 28c. Junction part 42 has a holding hole capable of holding container 15. Container 15 after the secondary BF separation process is transported to junction part 42. Junction part 42 is situated in an overlap region where second operation range 12a of container transferring mechanism 36 and operation range 37a of container transferring mechanism 37 overlap each other. Container 15 is passed between container transferring mechanism 36 and container transferring mechanism 37 at junction part 42.

R4-R5 reagent dispensing mechanism 33 includes R4 reagent nozzle 33a and R5 reagent nozzle 33b. R4 reagent nozzle 33a and R5 reagent nozzle 33b discharge the R4 reagent and the R5 reagent into container 15, respectively. The R4 reagent includes dispersion liquid and the R5 reagent includes a luminescent substrate.

Inter-level transporter 34 has a holding hole capable of holding container 15. Inter-level transporter 34 is raised and lowered between first level 21a and second level 21b by later-described elevating device 44. Inter-level transporter 34 and elevating device 44 allow transfer of container 15 between first level 21a and second level 21b.

Each of container transferring mechanisms 35, 36, and 37 has the function of holding container 15 and transporting it to a given component. All of container transferring mechanisms 35, 36, and 37 are cartesian coordinate robot mechanisms capable of moving along three orthogonal axes, namely, two horizontal axes and one vertical axis. The structures of container transferring mechanisms 35, 36, and 37 are basically the same, and a publically known structure can be employed. In the following, only container transferring mechanism 36 is described, and description of container transferring mechanisms 35 and 37 is omitted.

As illustrated in FIG. 3, container transferring mechanism 36 includes X-direction moving mechanism 51, Y-direction moving mechanism 52, and vertical-direction (Z-direction) moving mechanism 53. Moving mechanism 51, moving mechanism 52, and moving mechanism 53 include X-axis motor 54, Y-axis motor 55, and Z-axis motor 56, respectively. Container transferring mechanism 36 also includes catcher 57 that grasps container 15. Catcher 57 is capable of moving in the three, X-, Y-, and Z-axis directions by means of moving mechanism 51, moving mechanism 52, and moving mechanism 53. Container transferring mechanism 36 is capable of horizontally moving within second operation range 12a.

Second operation range 12a covers reaction part 28b, magnetic gathering port 38, R3 dispensing port 40, separation process part 32, and junction part 42. A region in second operation range 12a which covers R3 dispensing port 40 is overlap region 16 where second operation range 12a overlaps first operation range 11a of first reagent dispensing mechanism 31. The remaining region is non-overlap region 17b where second operation range 12a does not overlap first operation range 11a.

Container transferring mechanism 36 preferably transfers container 15 after the R3 reagent dispensing process to reaction part 28b and transfers container 15 after the reaction from reaction part 28b to separation process part 32 through a path that passes through overlap region 16. By employing this transfer path which allows container transferring mechanism 36 to move back and forth between reaction part 28b and separation process part 32 through overlap region 16, there is no need to arrange reaction part 28b and separation process part 32 adjacently to each other or provide multiple reaction parts 28b and multiple separation process parts 32 so as to make a transfer path that does not pass through overlap region 16. This allows improvement in the freedom in the layout of reaction part 28b and separation process part 32 as well as first reagent dispensing mechanism 31 and other components. Moreover, even when an abnormality occurs in first reagent dispensing mechanism 31 at overlap region 16, first reagent dispensing mechanism 31 can be retreated to non-overlap region 17a, and the transferring process by container transferring mechanism 36 can therefore be continued.

Also, in the embodiment, container transferring mechanism 36 transfers container 15 after the R2 reagent dispensing process by second reagent dispensing mechanism 30 to separation process part 32, and moves container 15 after the separation process by separation process part 32 to overlap region 16. Then, first reagent dispensing mechanism 31 performs the dispensing process of dispensing the R3 reagent into container 15 transferred by container transferring mechanism 36 from separation process part 32 to overlap region 16. In this way, there is no need to arrange second reagent dispensing mechanism 30 and separation process part 32 adjacently to each other so as to make a transfer path that does not pass through overlap region 16.

Also, in the embodiment, container transferring mechanism 36 transfers container 15 after the R2 reagent dispensing process by second reagent dispensing mechanism 30 to reaction part 28b and transfers container 15 after the reaction to separation process part 32 through the path which passes through overlap region 16. This allow improvement in the freedom in the layout of each component of second reagent dispensing mechanism 30, reaction part 28b, separation process part 32, and first reagent dispensing mechanism 31. Thus, although container transferring mechanism 36 passes through overlap region 16 back and forth, the repetitive transferring process by container transferring mechanism 36 can be continued when an abnormality occurs in first reagent dispensing mechanism 31 at overlap region 16.

Meanwhile, referring back to FIG. 2, container transferring mechanism 35 is capable of moving within operation range 35a while holding container 15. Operation range 35a covers reaction part 28a, R2 dispensing port 39, and magnetic gathering port 38. Container transferring mechanism 37 is capable of moving within operation range 37a while holding container 15. Operation range 37a covers junction part 42, reaction part 28c, R4-R5 reagent dispensing mechanism 33, and inter-level transporter 34.

Figure 4:
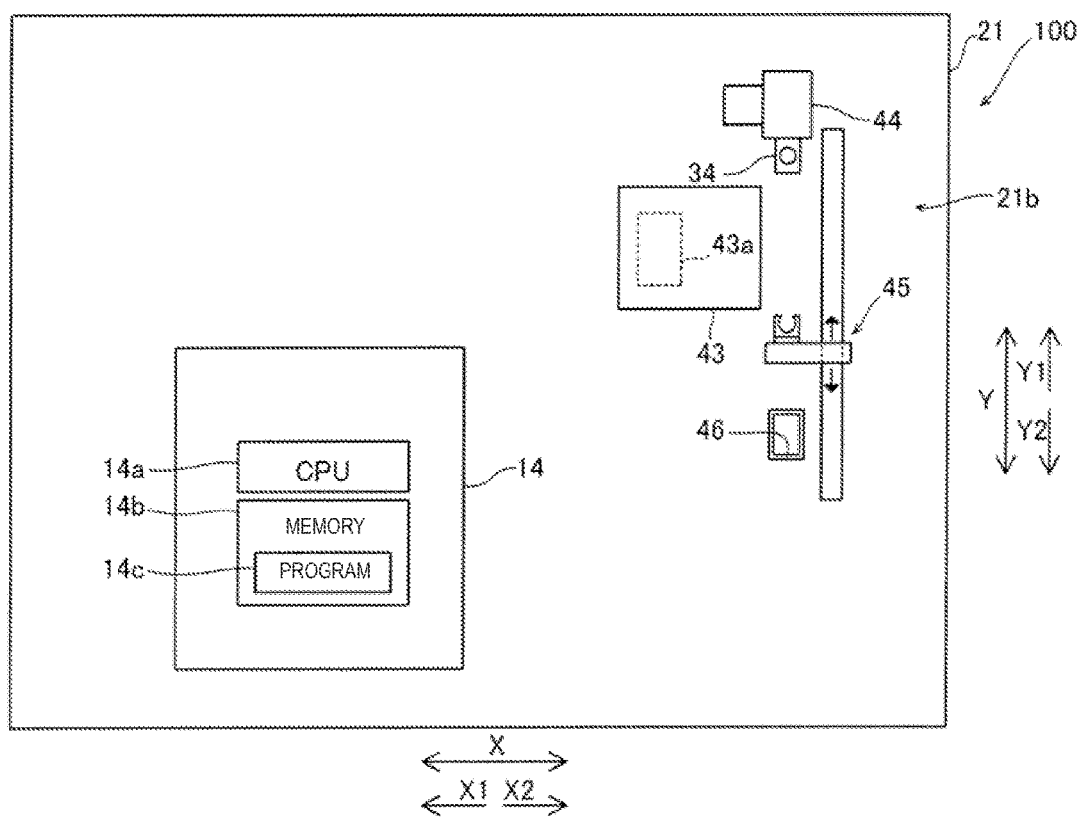
FIG. 4 is a schematic plan view illustrating a second level of the sample processing apparatus according to an embodiment.

Next, the configuration of each component set at second level 21b is described with reference to FIG. 4.

At second level 21b of housing 21, sample processing apparatus 100 includes measuring part 43, elevating device 44, container transporter 45, container discarding hole 46, and controller 14. As described, in the embodiment, measuring part 43 is arranged at second level 21b situated below first level 21a. The installation area of sample processing apparatus 100 can be reduced by disposing first mechanism unit 11 (first reagent dispensing mechanism 31) and second mechanism unit 12 (container transferring mechanism 36) at first level 21a and disposing measuring part 43 at second level 21b. Even in this case, overlap region 16 can be provided in the operation range of each of first mechanism unit 11 and second mechanism unit 12, and a sufficiently high freedom can be ensured for the layout.

Container transporter 45 transports container 15 between inter-level transporter 34 lowered to second level 21b, measuring part 43, and container discarding hole 46.

Measuring part 43 includes light detector 43a such as a photomultiplier tube. Measuring part 43 measures the amount of the antigen included in the sample on which the various processes have been performed, by obtaining light generated in the course of the reaction between the labeled antibody, which has bound to the antigen of the sample, and the luminescent substrate by means of light detector 43a.

Controller 14 includes a personal computer (PC) which includes CPU 14a, memory 14b, and the like. The PC functions as a controller of sample processing apparatus 100 with CPU 14a running control program 14c stored in memory 14b. As mentioned above, controller 14 performs control which detects an abnormality in first mechanism unit 11 based on the result of detection by operation detector 13, control which causes first mechanism unit 11 to retreat to non-overlap region 17a, and control which causes second mechanism unit 12 to continue the second process. Moreover, controller 14 controls the operation of each component of sample processing apparatus 100 described above.

Figure 5:
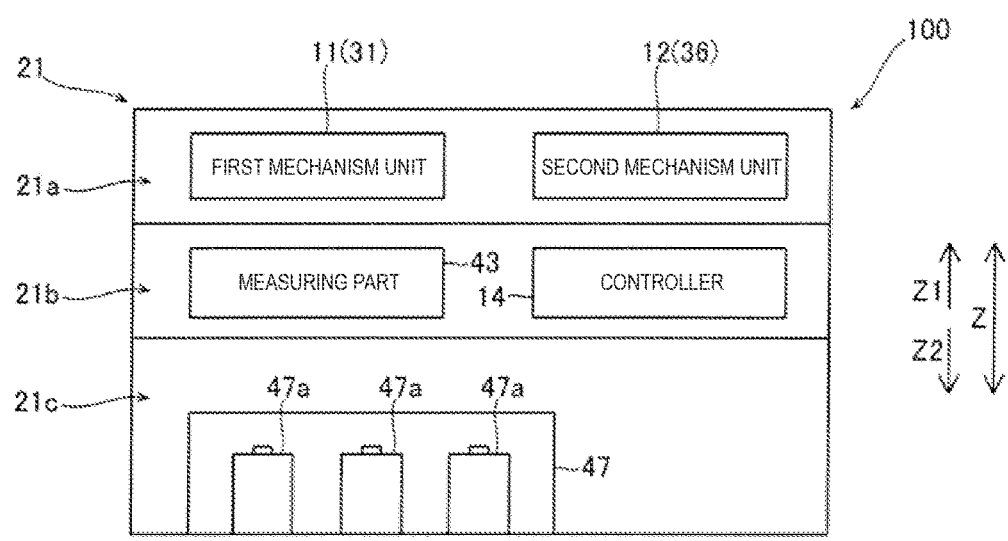
FIG. 5 is a schematic side view for describing the multi-level structure of the sample processing apparatus according to an embodiment.

Note that as illustrated in FIG. 5, sample processing apparatus 100 includes container housing part 47 at third level 21c of housing 21. Cleaning liquid containers 47a that contain the cleaning liquid are set in container housing part 47. The cleaning liquid in each cleaning liquid container 47a is supplied to cleaner 41 at first level 21a through a fluid circuit not illustrated. Liquid containers other than cleaning liquid containers 47a may be set in container housing part 47.

[Structures of Reagent Dispensing Mechanisms]

Next, details of the structure of first reagent dispensing mechanism 31 are described with reference to FIGS. 6 and 3. Note that the structures of third reagent dispensing mechanism 29 and second reagent dispensing mechanism 30 are basically the same as the structure of first reagent dispensing mechanism 31.

Figure 6:
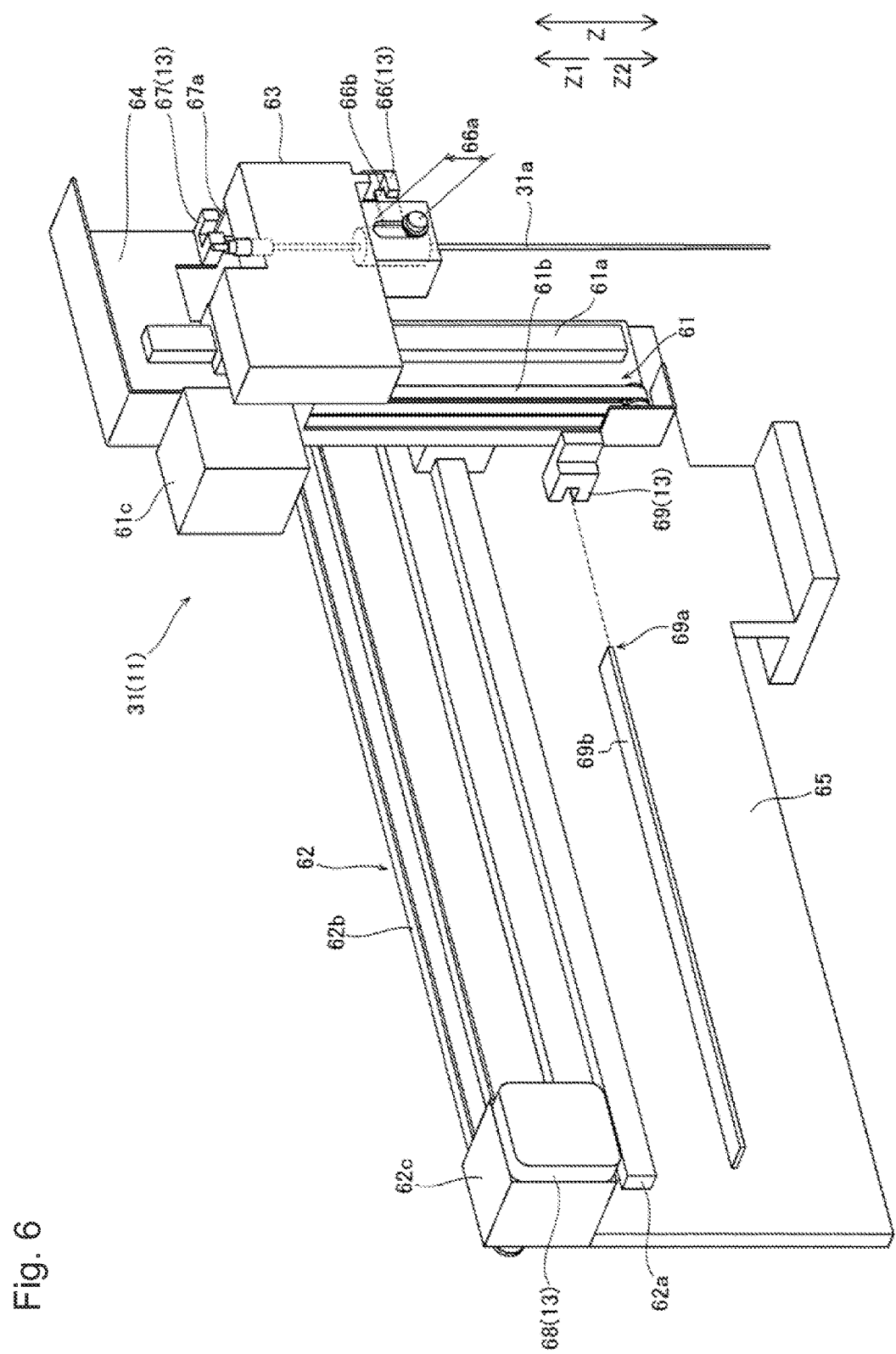
FIG. 6 is a perspective view illustrating the reagent dispensing mechanism of the sample processing apparatus according to an embodiment.

As illustrated in FIG. 6, first reagent dispensing mechanism 31 includes; pipette 31a that dispenses the reagent; elevating mechanism 61 that vertically moves pipette 31a; and horizontally moving mechanism 62 that linearly moves between the reagent aspirating position (i.e. aspirating hole 27h) and the reagent dispensing position (i.e. R3 dispensing port 40).

Pipette 31a is attached to holding member 63. An upper end portion of pipette 31a is connected to a fluid circuit not illustrated. Elevating mechanism 61 includes rail 61a that guides rising and lowering movement of holding member 63, transmission mechanism 61b coupled to holding member 63, and motor 61c for the raising and lowering. Transmission mechanism 61b is, for example, a belt-pulley mechanism, and holding member 63 is coupled to a part of its annular belt. Motor 61c is, for example, a stepper motor and connected to the pulley of transmission mechanism 61b. By vertically moving the belt of transmission mechanism 61b with the drive force of motor 61c, holding member 63 is raised or lowered along with pipette 31a. Elevating mechanism 61 is provided to holding member 64.

Horizontally moving mechanism 62 includes: rail 62a that guides horizontal movement of holding member 64; transmission mechanism 62b coupled to holding member 64; and motor 62c for the horizontal movement that applies drive force to transmission mechanism 62b. Motor 62c is a motor that moves first reagent dispensing mechanism 31 between overlap region 16 (see FIG. 3) and non-overlap region 17a (see FIG. 3). Transmission mechanism 62b is, for example, a belt-pulley mechanism. Motor 62c is, for example, a stepper motor. By horizontally moving the belt of transmission mechanism 62b with the drive force of motor 62c, holding member 64, holding member 63, and pipette 31a linearly horizontally move together. Horizontally moving mechanism 62 is provided to support member 65.

Operation detector 13, which detects the operation of first reagent dispensing mechanism 31, preferably includes collision detecting sensor 66 that detects collision of pipette 31a. Collision detecting sensor 66 is, for example, a photointerrupter. Collision detecting sensor 66 is fixed to holding member 63. Holding member 63 supports pipette 31a such that pipette 31a can be vertically moved relative to holding member 63 within predetermined range 66a. Pipette 31a is biased downward by a biasing member not illustrated to be situated at the lower end position in predetermined range 66a. Pipette 31a is provided with detection member 66b that shades collision detecting sensor 66 from light. Collision detecting sensor 66 is normally in the shaded state. When the tip of pipette 31a collides with some object while holding member 63 is being lowered, pipette 31a is pushed upward within predetermined range 66a. As a result, detection member 66b is displaced upward from the shading position, so that collision detecting sensor 66 switches to a light transmitting state.

In addition, operation detector 13 preferably includes first base point sensor 67 which detects that pipette 31a is at an upper base point position in the vertical direction. First base point sensor 67 is arranged at the upper base point position. First base point sensor 67 is, for example, a photointerrupter provided to holding member 64. Holding member 63 is provided with detection member 67a that shades first base point sensor 67 from light at the upper base point position. When holding member 63 is raised in a Z1 direction and reaches the upper base point position, first base point sensor 67 switches from a light transmitting state to the shaded state. Based on the change in a detection signal from first base point sensor 67, controller 14 detects that holding member 63 and pipette 31a have reached the upper base point position.

In addition, operation detector 13 preferably includes encoder 68 that detects the rotational position of motor 62c. Encoder 68 is attached to motor 62c and detects the actual amount of rotation of motor 62c when it is driven. Based on a detection signal from encoder 68, controller 14 horizontally moves pipette 31a to the reagent aspirating position or the reagent dispensing position.

In addition, operation detector 13 preferably includes second base point sensor 69 which detects that first reagent dispensing mechanism 31 is at horizontal base point position 69a within non-overlap region 17a in the horizontal direction. Second base point sensor 69 is, for example, a photointerrupter provided to holding member 64. Support member 65 is provided with detection member 69b. When holding member 64 is horizontally moved and reaches horizontal base point position 69a, second base point sensor 69 switches from a light transmitting state to a shaded state by detection member 69b. Based on the change in a detection signal from second base point sensor 69, controller 14 detects that holding member 64, holding member 63, and pipette 31a have reached horizontal base point position 69a. Note that horizontal base point position 69a is arranged in non-overlap region 17a.

Horizontal base point position 69a is preferably a retreating position used when an abnormality occurs. Specifically, upon detection of an abnormality in first reagent dispensing mechanism 31, controller 14 causes first reagent dispensing mechanism 31 to retreat to horizontal base point position 69a based on the result of detection by second base point sensor 69. Thus, when an abnormality is detected in first reagent dispensing mechanism 31, it is possible to detect that first reagent dispensing mechanism 31 has retreated to horizontal base point position 69a in non-overlap region 17a. Hence, the transferring process by container transferring mechanism 36 can be continued, with a confirmation that the retreating operation is properly completed and no interference is therefore occurring.

More preferably, as illustrated in FIG. 3, cleaner 41, which cleans first reagent dispensing mechanism 31 after its dispensing process, is provided at horizontal base point position 69a. In this way, the retreating position used when an abnormality is detected can also serve as the cleaning position during the normal operation. Thus, there is no need to additionally provide a base point sensor exclusively for the retreating operation performed when an abnormality is detected. This can accordingly prevent an increase in the number of components for the positional detection in the retreating operation performed when an abnormality is detected.

[Operation of Sample Processing Apparatus in Measurement Process]

Next, the operation of sample processing apparatus 100 in a measurement process is described with reference to FIGS. 2 and 7.

The measurement operation is briefly described. Sample processing apparatus 100 firstly causes a capture antibody to bind to an antigen included in a sample via antigen-antibody reaction, and causes a magnetic particle to bind to the capture antibody which has bound to the antigen. Then, sample processing apparatus 100 performs the primary BF separation process to magnetically collect the complex of the bound antigen, capture antibody, and magnetic particle and to remove the unreacted capture antibody. Then, sample processing apparatus 100 causes a labeled antibody to bind to the complex and thereafter performs the secondary BF separation process to magnetically collect the complex of the bound magnetic particle, antigen, and labeled antibody and to remove the unreacted labeled antibody. Then, sample processing apparatus 100 adds a dispersion liquid and a luminescent substrate and thereafter measures the amount of light emission resulting from the reaction between the labeled antibody and the luminescent substrate. Through these steps to quantitatively measure the antigen in the sample which has bound to the labeled antibody, sample processing apparatus 100 allows analyses on the sample for different analysis items.

Figure 7:
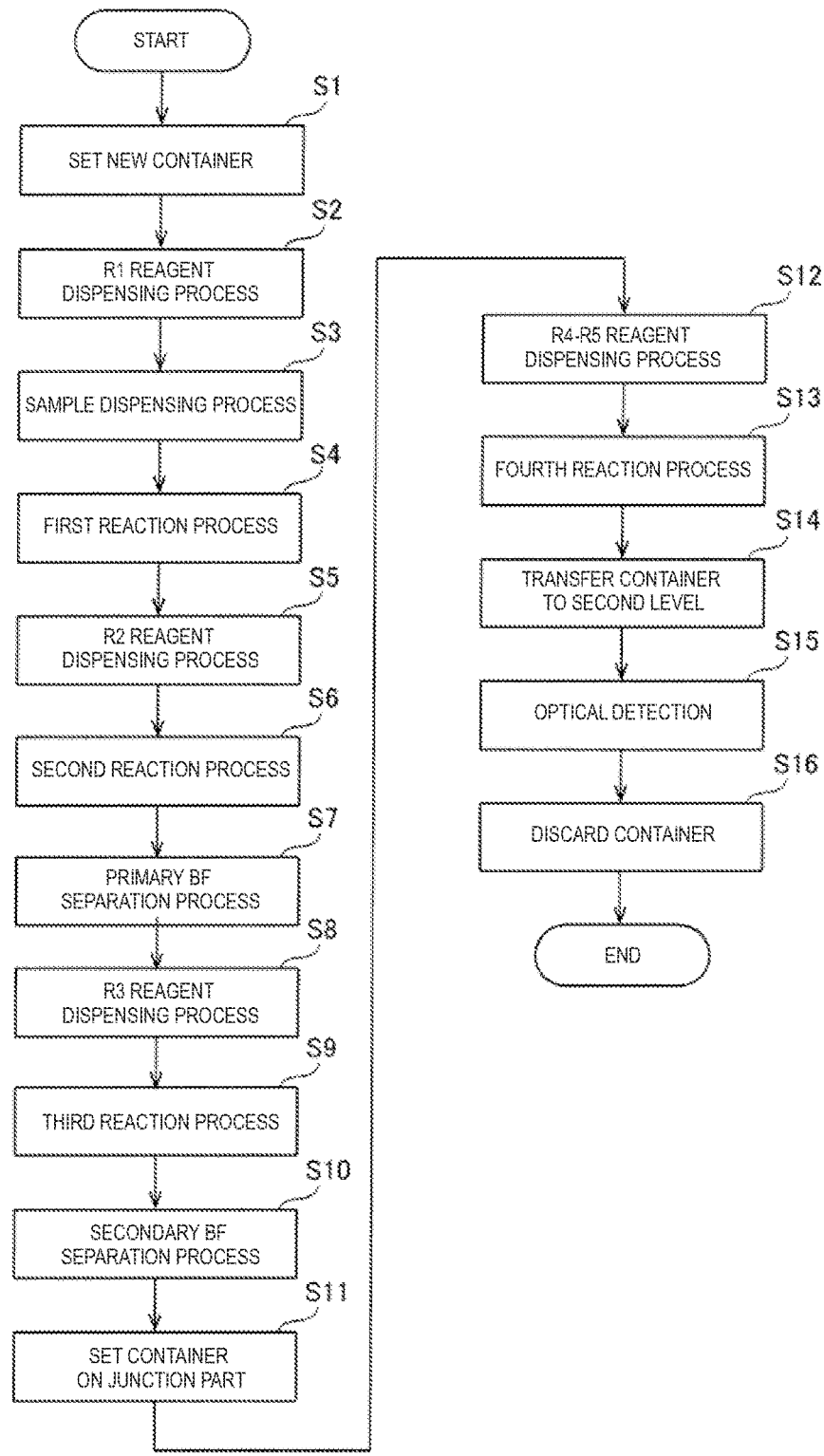
FIG. 7 is a flowchart for describing operation in a measurement process.

Next, the operation of sample processing apparatus 100 in the measurement process is described using a flowchart in FIG. 7. Note that controller 14 (see FIG. 4) controls the operation of sample processing apparatus 100. In actual practice, the process operation is performed on the samples in multiple containers 15 simultaneously and continuously, but only the analysis process on the sample in one container 15 is described below. In the following description, each component of sample processing apparatus 100 refers to FIG. 2 or 4.

First, in step S1, container supplying mechanism 25 sets new container 15 on container transporter 26. In step S2, container transporter 26 transports container 15 to R1 reagent dispensing position 26b, and third reagent dispensing mechanism 29 dispenses the R1 reagent into container 15. In step S3, container transporter 26 transports container 15 to sample dispensing position 26a, and sample dispensing mechanism 23 dispenses a sample aspirated from test tube 22a into container 15.

In step S4, container transporter 26 transports container 15 to container unloading position 26c, and container transferring mechanism 35 takes out container 15 and sets it on reaction part 28a. In this state, the first reaction process is performed which heats the sample and the R1 reagent in container 15 for a predetermined time to a predetermined temperature.

In step S5, container transferring mechanism 35 transports container 15 from reaction part 28a to R2 dispensing port 39, and second reagent dispensing mechanism 30 dispenses the R2 reagent into container 15. In step S6, container transferring mechanism 35 takes out container 15 from R2 dispensing port 39 and sets it on reaction part 28a. In this state, the second reaction process is performed which heats the sample, the R1 reagent, and the R2 reagent in container 15 for a predetermined time to a predetermined temperature.

In step S7, the primary BF separation process is performed. Specifically, container transferring mechanism 35 transports container 15 from reaction part 28a to magnetic gathering port 38. At magnetic gathering port 38, the magnetic particles in container 15 are magnetically gathered by means of a magnet. Then, container transferring mechanism 36 transports container 15 from magnetic gathering port 38 to separation process part 32. Separation process part 32 magnetically collects the complex of the antigen, the R1 reagent, and the R2 reagent in container 15 and removes the unreacted R1 reagent.

In step S8, container transferring mechanism 36 transports container 15 from separation process part 32 to R3 dispensing port 40. First reagent dispensing mechanism 31 moves to R3 dispensing port 40 and dispenses the R3 reagent into container 15. After the dispensing, first reagent dispensing mechanism 31 moves to cleaner 41.

In step S9, container transferring mechanism 36 takes out container 15 from R3 dispensing port 40 and sets it on reaction part 28b. In this state, the third reaction process is performed which heats the sample, the R1 reagent, the R2 reagent, and the R3 reagent in container 15 for a predetermined time to a predetermined temperature.

In step S10, the secondary BF separation process is performed. Specifically, container transferring mechanism 36 transports container 15 from reaction part 28b to magnetic gathering port 38 to magnetically gather the magnetic particles in container 15. Then, container transferring mechanisms 36 transports container 15 from magnetic gathering port 38 to separation process part 32 through overlap region 16. Separation process part 32 magnetically collects the complex of the antigen, the R1 reagent, the R2 reagent, and the R3 reagent in container 15 and removes the unreacted R3 reagent.

In step S11, container transferring mechanism 36 transports container 15 from separation process part 32 to junction part 42.

In step S12, the R4 reagent and the R5 reagent are dispensed. Container transferring mechanism 37 takes out container 15 from junction part 42 and transports it to R4-R5 reagent dispensing mechanism 33. R4-R5 reagent dispensing mechanism 33 sequentially dispenses the R4 reagent and the R5 reagent into container 15.

In step S13, container transferring mechanism 37 sets container 15 on reaction part 28c. In this state, the fourth reaction process is performed which heats the sample and the R1 to R5 reagents in container 15 for a predetermined time to a predetermined temperature. By this fourth reaction process, the process of preparing a measurement specimen is completed.

In step S14, container transferring mechanism 37 takes out container 15 from reaction part 28c and sets it on inter-level transporter 34. Then, elevating device 44 lowers inter-level transporter 34 to transport container 15 to second level 21b (see FIG. 4).

In step S15, optical detection is performed. Specifically, container transporter 45 takes out container 15 from inter-level transporter 34 and transports it to measuring part 43. Measuring part 43 measures the amount of the antigen included in the sample. In step S16 after the optical detection, container transporter 45 takes out container 15, for which the measurement is done, from measuring part 43 and discards it into container discarding hole 46. By this step, the operation of sample processing apparatus 100 in the measurement process is done.

[Operation of Sample Processing Apparatus upon Detection of an Abnormality]

Figure 8:
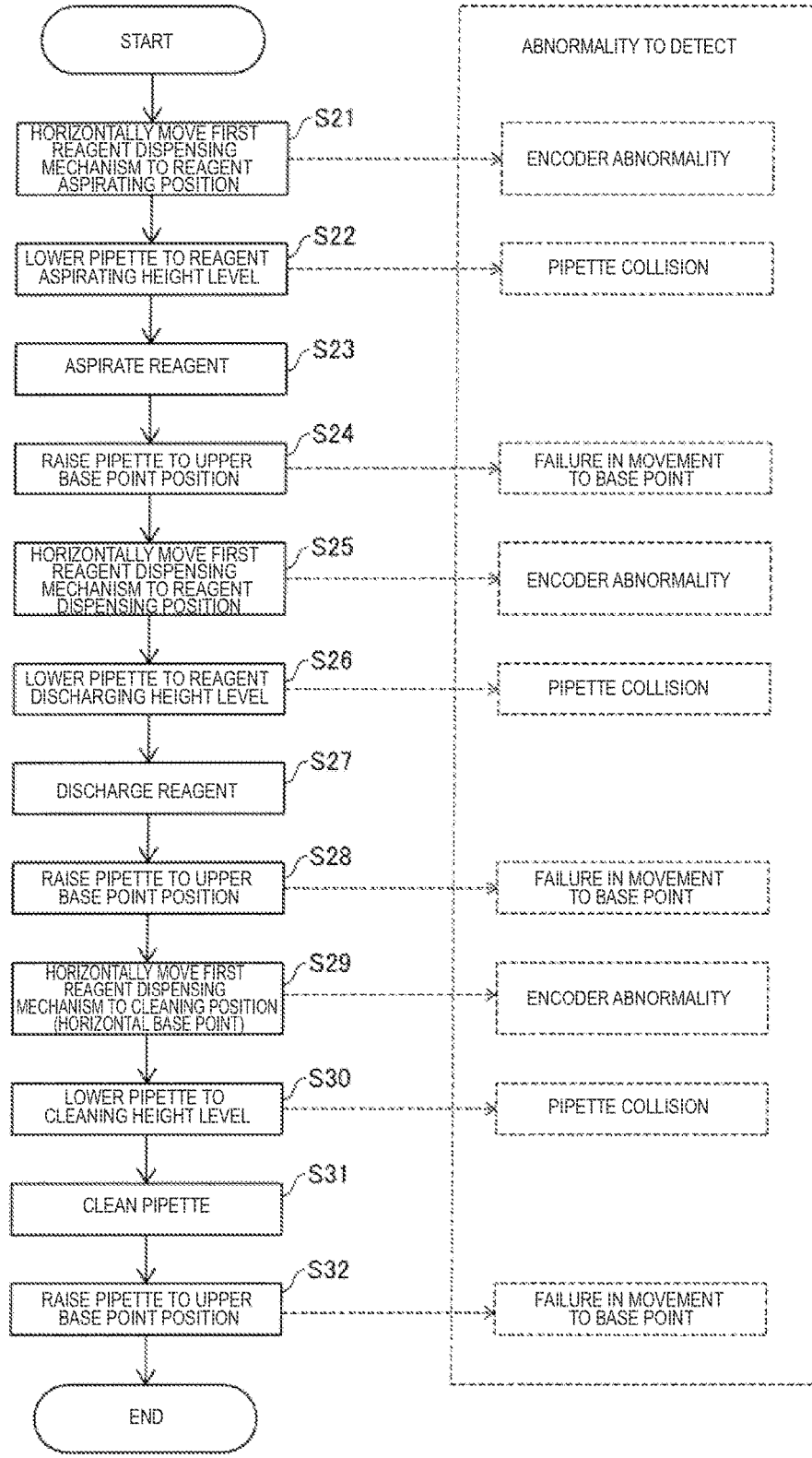
FIG. 8 is a flowchart for describing operation in an R3 reagent dispensing process.

Next, the operation of sample processing apparatus 100 upon detection of an abnormality is described. The following describes a case where controller 14 detects an abnormality during the dispensing operation of first reagent dispensing mechanism 31. A process for R3 reagent dispensing operation illustrated in FIG. 8 is the process performed by first reagent dispensing mechanism 31 in step S8 in FIG. 7. In the following, each component of first reagent dispensing mechanism 31 refers to FIG. 6, and each position related to the movement of first reagent dispensing mechanism 31 refers to FIG. 3.

In step S21, controller 14 horizontally moves first reagent dispensing mechanism 31 to the reagent aspirating position (i.e. aspirating hole 27h).

In step S22, controller 14 lowers pipette 31a to a predetermined reagent aspirating height level. In step S23, controller 14 causes pipette 31a to aspirate the R3 reagent.

In step S24, controller 14 raises pipette 31a to the upper base point position.

In step S25, controller 14 horizontally moves first reagent dispensing mechanism 31 to the R3 reagent dispensing position (R3 dispensing port 40). In this step, first reagent dispensing mechanism 31 enters overlap region 16 in first operation range 11a.

In step S26, controller 14 lowers pipette 31a to a predetermined reagent discharging height level. In step S27, controller 14 causes pipette 31a to discharge the R3 reagent. In step S28, controller 14 raises pipette 31a to the upper base point position.

In step S29, controller 14 horizontally moves first reagent dispensing mechanism 31 to horizontal base point position 69a (cleaner 41). In step S30, controller 14 lowers pipette 31a to a predetermined cleaning height level. In step S31, controller 14 causes pipette 31a to perform cleaning operation.

In step S32, controller 14 raises pipette 31a to the upper base point position. By the above step, the dispensing operation of first reagent dispensing mechanism 31 is done.

In each of steps S21, S25, and S29, controller 14 detects an abnormality if the detection value of encoder 68 is outside an allowable range. Specifically, controller 14 detects an abnormality in the movement of first reagent dispensing mechanism 31 between overlap region 16 and non-overlap region 17a if the amount by which motor 62c is actually driven (i.e. actual rotation pulse number) in response to a command value given to motor 62c by controller 14 (i.e. command pulse number) is outside an allowable range. In this way, it is possible to detect an abnormality which prevents proper movement between overlap region 16 and non-overlap region 17a during the dispensing process and to quickly retreat first reagent dispensing mechanism 31 to non-overlap region 17a.

Also, in each of steps S22, S26, and S30, controller 14 detects collision of pipette 31a as an abnormality in first reagent dispensing mechanism 31 upon a change in a detection signal from collision detecting sensor 66. The collision of pipette 31a is an abnormality that occurs due to a factor such as the presence of an object placed by mistake at the position to which pipette 31a is lowered, displacement of the horizontal position of pipette 31a from the position to which it is lowered, bending of pipette 31a, or tilting of holding member 63, for example. In this way, it is possible to detect an abnormality which prevents first reagent dispensing mechanism 31 from properly performing its dispensing process and to quickly retreat first reagent dispensing mechanism 31 to non-overlap region 17a.

Also, in each of steps S24, S28, and S32, controller 14 detects a base point return abnormality which is an abnormality in returning to the upper base point position based on the detection signal from first base point sensor 67. Controller 14 detects that pipette 31a has failed to return to the base point at the upper base point position, if the operation of raising pipette 31a is performed but pipette 31a does not reach the upper base point position or if the timing at which pipette 31a reaches the upper base point position is before or after an allowable range. In this way, it is possible to detect an abnormality which prevents the proper raising-lowering operation of first reagent dispensing mechanism 31 involved in its dispensing process and to quickly retreat first reagent dispensing mechanism 31 to non-overlap region 17a.

As described above, the presence of an abnormality is determined while each step is performed. If detecting an abnormality in any of the steps, controller 14 stops the current and subsequent steps and performs a later-described abnormality responding process. Controller 14 therefore performs the process of the next step only when no abnormality is detected during the operation of the current step.

Note that operation detector 13 may include a sensor that detects discharge of the reagent by first reagent dispensing mechanism 31. In this case, controller 14 may detect an abnormality which prevents first reagent dispensing mechanism 31 from properly performing its dispensing process based on the result of detection of discharge of the reagent by first reagent dispensing mechanism 31.

[Abnormality Responding Process in Sample Processing Apparatus]

Figure 9:
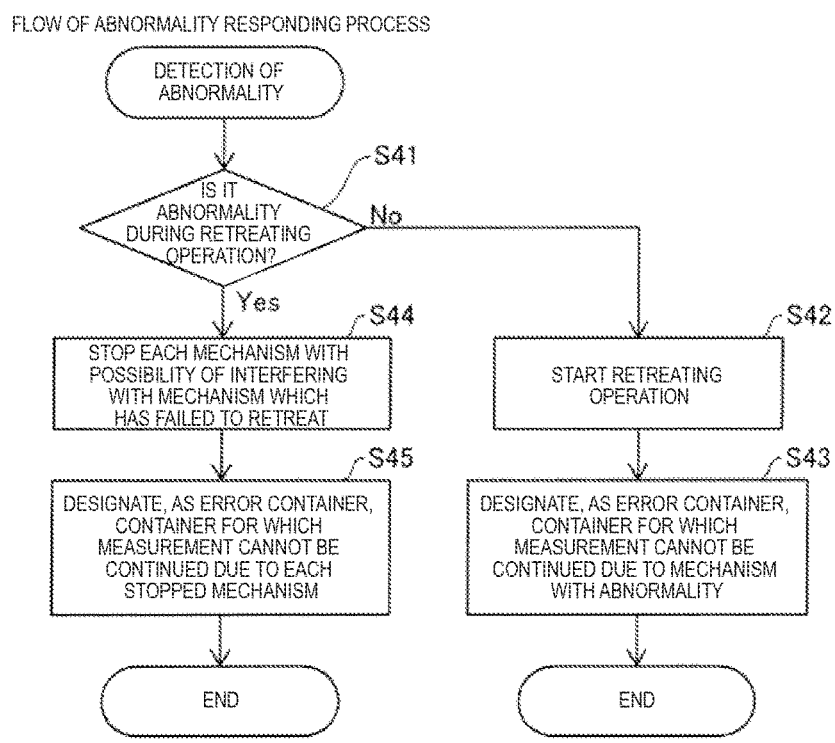
FIG. 9 is a flowchart for describing the operation of a controller in an abnormality responding process.
Figure 10:
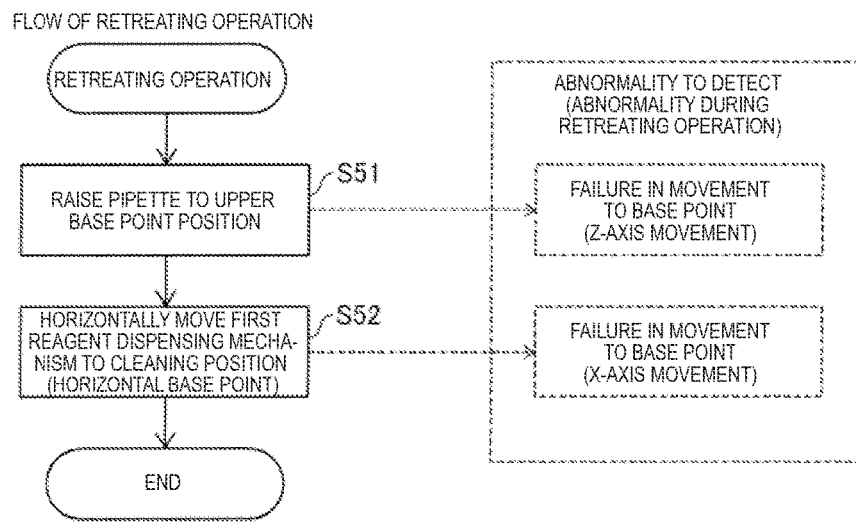
FIG. 10 is a flowchart for describing a retreating operation.

Next, an abnormality responding process in sample processing apparatus 100 is described using flowcharts in FIGS. 9 and 10. The abnormality responding process illustrated in FIG. 9 is a process performed as an interrupt process when controller 14 detects an abnormality as illustrated in some steps in FIG. 8. The following describes an abnormality responding process performed when controller 14 detects an abnormality in first reagent dispensing mechanism 31.

In step 41 in FIG. 9, controller 14 determines whether or not the abnormality detected this time is an abnormality during the retreating operation. Controller 14 advances the process to step S42 if the abnormality detected this time is an abnormality detected during the normal analysis operation in sample processing apparatus 100 as illustrated in FIG. 8.

In step S42, controller 14 starts the retreating operation of the mechanism in which the abnormality is detected. In step S51 in FIG. 10, controller 14 raises pipette 31a to the upper base point position. Then, in step S52, controller 14 horizontally moves first reagent dispensing mechanism 31 to horizontal base point position 69a. As a result, first reagent dispensing mechanism 31 exits overlap region 16 and retreats to horizontal base point position 69a in non-overlap region 17a (see FIG. 3). Thus, container transferring mechanism 36 continues its transferring process.

After starting the retreating operation in step S42 in FIG. 9, controller 14 advances the process to step S43. In step S43, controller 14 designates, as an error container, container 15 for which the measurement cannot be continued due to the mechanism with the abnormality.

Container 15 for which the measurement cannot be continued due to the mechanism with the abnormality is container 15 being subjected to the process by the mechanism with the abnormality. In the case where the abnormality is detected during the dispensing process by first reagent dispensing mechanism 31, container 15 disposed at the R3 reagent dispensing position (R3 dispensing port 40) for dispensing the R3 reagent is designated as an error container. Container 15 designated as an error container is excluded from the rest of the measurement process.

In this case, containers 15 for which the R3 reagent dispensing process has already been completed by the time of the detection of the abnormality are still measurement targets. Specifically, containers 15 in which the R3 reagent has already been dispensed and which have already been set on reaction part 28b and separation process part 32 by the time of the detection of the abnormality continue to be transferred by container transferring mechanism 36, with first reagent dispensing mechanism 31 retreated to horizontal base point position 69a. Thus, containers 15 in which the R3 reagent has already been disposed by the time of the detection of the abnormality undergo the R4 and R5 reagent dispensing process and other processes in the downstream steps and complete the measurement process at measuring part 43.

Here, in the case of starting the retreating operation in step S42, controller 14 performs an abnormality detection also during the retreating operation in steps S51 and S52 illustrated in FIG. 10. In step S51, controller 14 detects whether or not there is a base point return abnormality which is an abnormality in returning to the upper base point position, based on the detection signal from first base point sensor 67. In step S52, controller 14 detects whether or not there is a base point return abnormality which is an abnormality in returning to the horizontal base point position, based on the detection signal from second base point sensor 69. Controller 14 advances the process from step S41 to step S44 in FIG. 9 if detecting an abnormality in first reagent dispensing mechanism 31 which is performing the retreating operation.

In step S44, controller 14 stops the operation of the mechanism which has failed to retreat due to the detected abnormality and the operation of the mechanism(s) having a possibility of interfering with that mechanism. Specifically, if the retreating operation of first reagent dispensing mechanism 31 fails, controller 14 stops both first reagent dispensing mechanism 31, which is first mechanism unit 11, and container transferring mechanism 36, which is second mechanism unit 12. In this case, controller 14 does not cause these mechanisms, of which the operations should be stopped, to perform their retreating operations but causes them to stop at their current positions when detecting the abnormality during the retreating operation.

Figure 11:
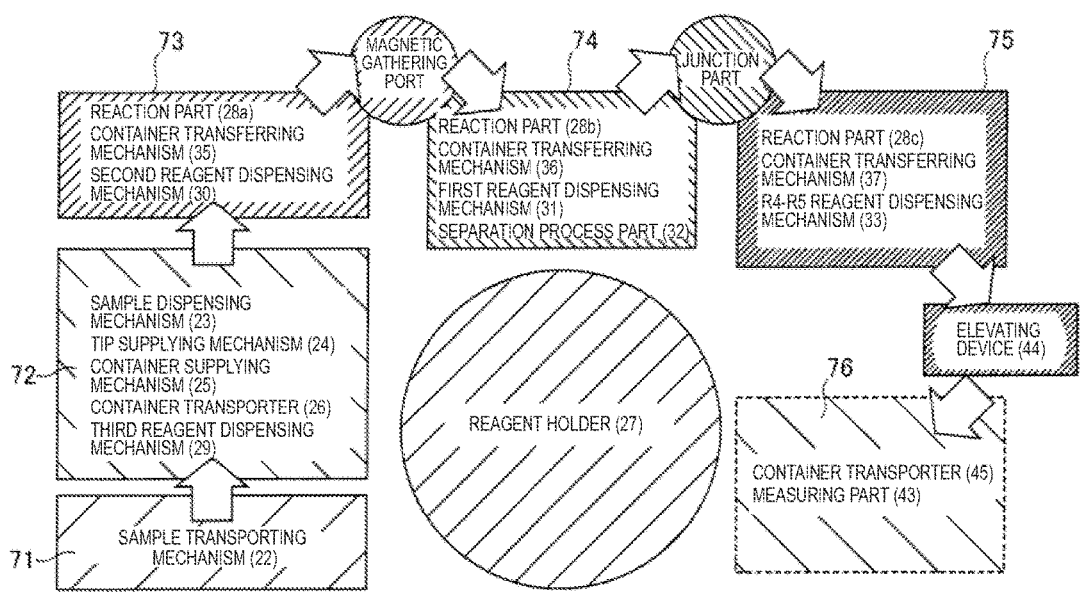
FIG. 11 is a schematic diagram for describing groups of mechanisms, each group of mechanisms being stopped when an abnormality is detected in the group.

Note that the grouping of mechanisms which have a possibility of interfering with a certain mechanism when it fails to retreat may be determined based on the operation ranges of the container transferring mechanisms. Specifically, as illustrated in FIG. 11, the mechanisms are divided into groups 71 to 76 based on the stages of their process steps. In sample processing apparatus 100, the set of mechanisms for which container transferring mechanism 35 is responsible for the container transfer, the set of mechanisms for which container transferring mechanism 36 is responsible for the container transfer, and the set of mechanisms for which container transferring mechanism 37 is responsible for the container transfer are groups 73, 74, and 75, respectively. When there is a mechanism that fails to retreat, the operations of all the mechanisms included in the group that mechanism belongs to may be stopped.

In this case, when the retreating operation of first reagent dispensing mechanism 31 fails, not only first reagent dispensing mechanism 31, which is first mechanism unit 11, and container transferring mechanism 36, which is second mechanism unit 12, are both stopped but also the mechanisms in group 74, which first reagent dispensing mechanism 31 belongs to, are all stopped. Specifically, when an abnormality is detected during the retreating operation of first reagent dispensing mechanism 31, first reagent dispensing mechanism 31, container transferring mechanism 36, reaction part 28b and separation process part 32 are stopped. With group 74 stopped, upstream groups 71 to 73 are also stopped.

After this, in step S45 in FIG. 9, controller 14 designates, as error containers, all containers 15 for which the measurement cannot be continued due to the stopped mechanisms. Specifically, controller 14 designates, as error containers, containers 15 for which the measurement cannot be continued due to the stoppage of first reagent dispensing mechanism 31, which is first mechanism unit 11, and the stoppage of container transferring mechanism 36, which is second mechanism unit 12. That is, when an abnormality is detected during the retreating operation of first reagent dispensing mechanism 31, controller 14 designates each container 15 to be transferred by container transferring mechanism 36 as an error container.

In other words, containers 15 in the range for which the measurement cannot be continued are containers 15 in group 74 illustrated in FIG. 11. Specifically, those containers designated as error containers are containers 15 to be subjected to the dispensing process by first reagent dispensing mechanism 31, containers 15 in the reaction process set on reaction part 28b, containers 15 set on separation process part 32, container 15 at magnetic gathering port 38, and container 15 at junction part 42.

In this case, the measurement operation is continued for containers 15 which are situated downstream of container transferring mechanism 36 and are to be transferred by container transferring mechanism 37. Thus, containers 15 which are in downstream groups 75 and 76 at the time of the detection of the abnormality undergo the R4 and R5 reagent dispensing process and other processes in the downstream steps and complete the measurement process at measuring part 43.

[Other Exemplary Configurations of First Mechanism Unit and Second Mechanism Unit]

In this embodiment, the example where first mechanism unit 11 includes first reagent dispensing mechanism 31 and second mechanism unit 12 includes container transferring mechanism 36 is specifically described. However, first mechanism unit 11 and second mechanism unit 12 may include other mechanisms.

Figure 12:
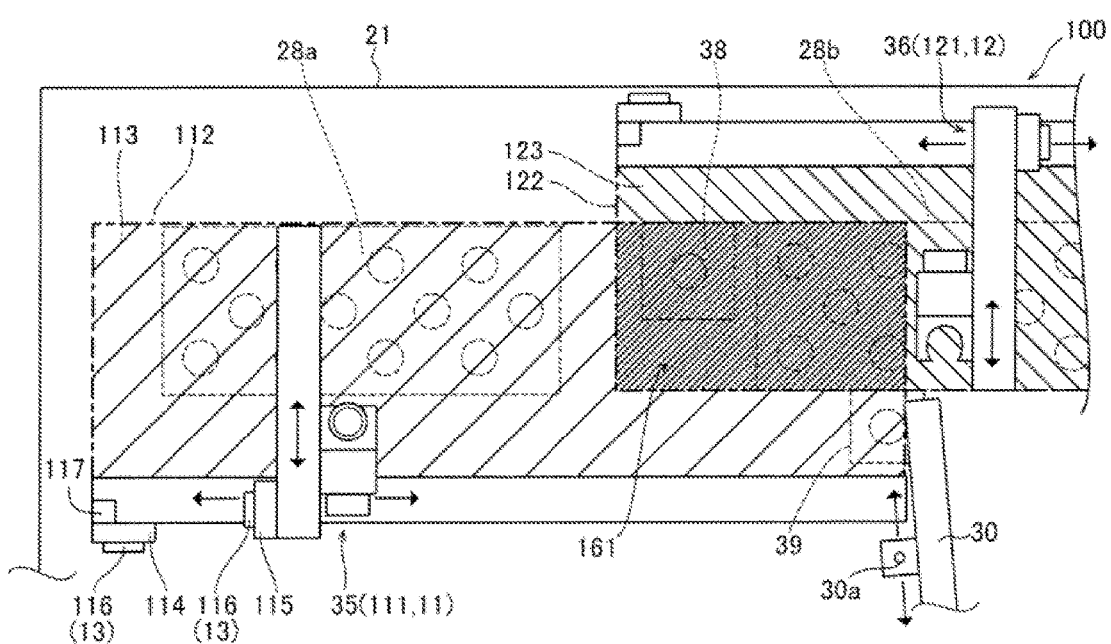
FIG. 12 is a schematic plan view illustrating another example of a first mechanism unit and a second mechanism unit.

Specifically, as illustrated in FIG. 12, first mechanism unit 11 may include first container transferring mechanism 111 that performs a transferring process of transferring container 15, and second mechanism unit 12 may include second container transferring mechanism 121 that performs a transferring process of transferring container 15 after completion of the transferring process by first container transferring mechanism 111. First container transferring mechanism 111 includes container transferring mechanism 35, for example, and second container transferring mechanism 121 includes container transferring mechanism 36, for example.

In this case, first operation range 112 of container transferring mechanism 35 and second operation range 122 of container transferring mechanism 36 include overlap region 161 where they overlap each other. First operation range 112 of container transferring mechanism 35 and second operation range 122 of container transferring mechanism 36 respectively include non-overlap regions 113 and 123 where they do not overlap each other. In this case, operation detector 13 includes encoders 116 for horizontal drive motors 114 and 115, respectively. Controller 14 detects an abnormality in container transferring mechanism 35 based on the result of detection with encoders 116. Upon detection of an abnormality in container transferring mechanism 35, controller 14 causes container transferring mechanism 35 to retreat to non-overlap regions 113 and causes container transferring mechanism 36 to continue its transferring process.

Preferably, the retreating position for container transferring mechanism 35 is a base point position arranged in non-overlap regions 113. More preferably, base point sensor 117 is provided at the base point position so that controller 14 can confirm whether the retreating operation is completed. With such a configuration, container transferring mechanism 35 can be retreated to non-overlap regions 113 even when an abnormality occurs while container transferring mechanism 35 transfers container 15 to R2 dispensing port 39 or magnetic gathering port 38 in overlap region 161, for example. Thus, container transferring mechanism 36 can continue its transferring process without interfering with container transferring mechanism 35.

Figure 13:
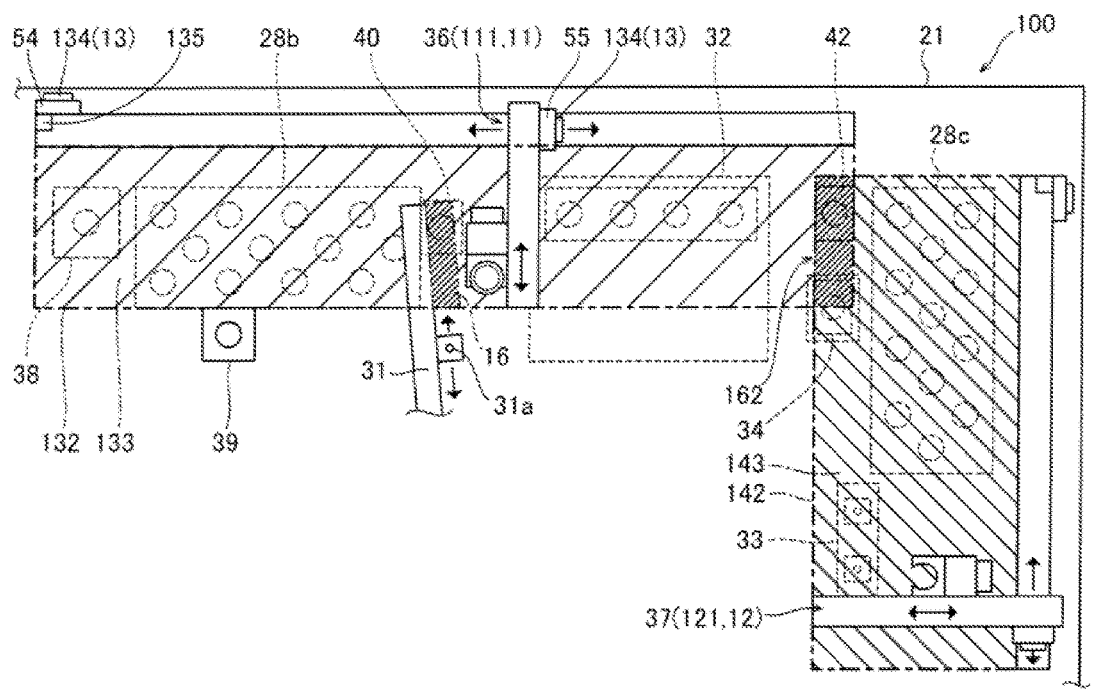
FIG. 13 is a schematic plan view illustrating still another example of the first mechanism unit and the second mechanism unit.

Alternatively, as illustrated in FIG. 13, first container transferring mechanism 111 may include container transferring mechanism 36 and second container transferring mechanism 121 may include container transferring mechanism 37. First operation range 132 of container transferring mechanism 36 and second operation range 142 of container transferring mechanism 37 include overlap region 162 where they overlap each other and respectively include non-overlap regions 133 and 143 where they do not overlap each other. Operation detector 13 includes encoders 134 for horizontal drive motors 54 and 55, respectively. Upon detection of an abnormality in container transferring mechanism 36 based on the result of detection with encoders 134, controller 14 causes container transferring mechanism 36 to retreat to non-overlap region 133 and causes container transferring mechanism 37 to continue its transferring process. The retreating position for container transferring mechanism 36 is preferably a base point position arranged in non-overlap region 133. Base point sensor 135 is provided at the base point position.

With such a configuration, container transferring mechanism 36 can be retreated to non-overlap region 133 even when an abnormality occurs while container transferring mechanism 36 is transferring container 15 to junction part 42 in overlap region 162. Thus, container transferring mechanism 37 can continue its transferring process without interfering with container transferring mechanism 36.

Besides the above, as illustrated in FIG. 12, first mechanism unit 11 may include second reagent dispensing mechanism 30, and second mechanism unit 12 may include container transferring mechanism 35. In this case, even when an abnormality occurs in second reagent dispensing mechanism 30 at R2 dispensing port 39, which is situated in the overlap region, second reagent dispensing mechanism 30 can be retreated to the non-overlap region and container transferring mechanism 35 can continue its transferring process.

Embodiments described above provide a sample processing apparatus capable of continuing a downstream process step even when an abnormality occurs in an upstream process step, and also of improving the freedom in the layout of mechanism units that perform these process steps.

Note that the embodiments disclosed herein are illustrative in every aspect and shall be considered to be not restrictive. The scope of embodiments is defined not by the description of the above embodiment but by the claims and further encompasses all modifications within the meaning and scope of equivalents of the claims.

The invention claimed is:

1. A sample processing apparatus, comprising:
a first reagent dispenser comprising a pipette, the first reagent dispenser having a first operation range of movement, the first reagent dispenser carrying out a first process on a container with a sample, the first operation range comprising an overlap region and a non-overlap region;
a container transfer comprising a holder for the container, the container transfer having a second operation range of movement, the container transfer carrying out a second process on the container after completion of the first process, the second operation range comprising the overlap region but not the non-overlap region;
a detector that senses operation of the first mechanism; and
a controller comprising a processor programmed to perform operations comprising:
causing the first reagent dispenser to stop the first process and retreat from the overlap region; and
causing the container transfer to continue the second process upon detection of abnormality in the first reagent dispenser by the detector.

2. The sample processing apparatus according to claim 1, wherein
the first reagent dispenser is coupled to the pipette, and
the container transfer moves the container after operation of the first reagent dispenser.

3. The sample processing apparatus according to claim 2, wherein the first reagent dispenser dispenses reagent into the container in the overlap region.

4. The sample processing apparatus according to claim 2, further comprising:
a reactor in which the container is held after the dispensing process and that allows reaction between the sample and the reagent in the container; and
a separator that separates unreacted components of the sample and the reagent from the container, wherein
the container transfer transfers the container to the reactor after the dispensing process and transfers the container from the reaction part to the separator, via a path that passes through the overlap region, after the reaction.

5. The sample processing apparatus according to claim 4, further comprising a second reagent dispenser that dispenses a second reagent into the container, wherein
the container transfer transfers the container to the separator after dispensing of the second reagent and moves the container after the separation process to the overlap region, and then
the first reagent dispenser dispenses the reagent into the container transferred from the separation process part to the overlap region by the container transfer.

6. The sample processing apparatus according to claim 5, wherein the container transfer transfers the container to the reactor after operation of dispensing of the reagent by the second reagent dispenser and then after reaction to the separator through the overlap region.

7. The sample processing apparatus according to claim 2, wherein
the pipette dispenses the reagent,
the first reagent dispenser includes an elevating mechanism that moves the pipette vertically,
the detector includes a collision detecting sensor that detects collision of the pipette, and
the processor of the controller is programmed to perform operations further comprising determining a collision abnormality of the pipette based on the detection result by the collision detecting sensor.

8. The sample processing apparatus according to claim 2, wherein
the pipette dispenses the reagent,
the first reagent dispenser includes an elevating mechanism that moves the pipette vertically,
the operation detector includes a first base point sensor that detects an upper base point position of the pipette in the vertical direction, and
the processor of the controller is programmed to perform operations further comprising detecting an abnormality related to return of the first reagent dispenser to the upper base point position, from output of the first base point sensor.

9. The sample processing apparatus according to claim 2, wherein
the first reagent dispenser includes a motor that moves the first regent dispenser between the overlap region and the non-overlap region,
the detector includes an encoder that detects a rotational position of the motor, and
the processor of the controller is programmed to perform operations further comprising detecting an abnormality related to movement of the first reagent dispenser between the overlap region and the non-overlap region, based on a result of detection with the encoder.

10. The sample processing apparatus according to claim 1, wherein
the detector includes a second base point sensor that detects a horizontal base point position of the first reagent dispenser in a horizontal direction in the non-overlap region, and
upon detection via the second base point sensor of the abnormality in the first-reagent dispenser, the processor of the controller is programmed to perform operations such that causing the first reagent dispenser to retreat to the horizontal base point position comprises causing the first mechanism to retreat based on the detection result by the second base point sensor.

11. The sample processing apparatus according to claim 10, wherein
the first reagent dispenser dispenses a reagent into the container by the pipette, and
the sample processing apparatus further comprises a cleaner at the base point position that cleans the first reagent dispenser after dispensing the reagent.

12. The sample processing apparatus according to claim 1, wherein the processor of the controller is programmed to perform operations further comprising stopping both the first reagent dispenser and the container transfer upon detection of an abnormality in the first reagent dispenser during a retreating operation of the first reagent dispenser to the non-overlap region.

13. The sample processing apparatus according to claim 1, wherein the container transfer further comprises
a mechanism that transfers the container, and
a mechanism that transfers the container after transfer of the container by the first reagent dispenser.

14. The sample processing apparatus according to claim 1, further comprising a light detector, wherein the light detector measures the sample after the second process by the container transfer, wherein
the first reagent dispenser and the container transfer are arranged at a first level, and
the light detector is arranged at a second level below the first level.

15. The sample processing apparatus according to claim 4, wherein
the reactor heats the sample and the reagent for a predetermined time to a predetermined temperature.

16. The sample processing apparatus according to claim 2, wherein the detector comprises a sensor that detects discharge of the reagent by the first reagent dispenser, and thereby allows the processor of the controller programmed to perform operations to detect an abnormality in the first reagent dispenser from detection of discharge of the reagent by the first reagent dispenser.

17. The sample processing apparatus according to claim 14, further comprising an inter-level transporter that transports the container from the first level to the second level.

* * * * *